United States Patent
Tran et al.

(10) Patent No.: US 10,549,127 B2
(45) Date of Patent: Feb. 4, 2020

(54) SELF-COOLING ULTRASOUND ABLATION CATHETER

(71) Applicant: Boston Scientific Scimed, Inc., Maple Grove, MN (US)

(72) Inventors: Binh C. Tran, Minneapolis, MN (US); Mark L. Jenson, Greenfield, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1274 days.

(21) Appl. No.: 14/032,929

(22) Filed: Sep. 20, 2013

(65) Prior Publication Data

US 2014/0088630 A1    Mar. 27, 2014

Related U.S. Application Data

(60) Provisional application No. 61/704,205, filed on Sep. 21, 2012.

(51) Int. Cl.
| | | |
|---|---|---|
| *A61N 7/02* | (2006.01) | |
| *A61N 7/00* | (2006.01) | |
| *A61B 17/22* | (2006.01) | |

(52) U.S. Cl.
CPC .......... *A61N 7/022* (2013.01); *A61B 17/2202* (2013.01); *A61N 2007/003* (2013.01); *A61N 2007/0043* (2013.01); *A61N 2007/0078* (2013.01)

(58) Field of Classification Search
CPC ........ A61B 17/2202; A61B 17/320068; A61B 8/4281; A61N 2007/003; A61N 2007/0078; A61N 7/022; A61N 7/02; A61N 2007/0056; A61N 2007/0065; A61N 2007/0069; A61N 2007/0091
See application file for complete search history.

(56) References Cited

U.S. PATENT DOCUMENTS

| | | |
|---|---|---|
| 164,184 A | 6/1875 | Kiddee |
| 1,167,014 A | 1/1916 | O'Brien |
| 2,505,358 A | 4/1950 | Gusberg |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |

(Continued)

FOREIGN PATENT DOCUMENTS

| | | |
|---|---|---|
| DE | 10038737 A1 | 2/2002 |
| EP | 1053720 A1 | 11/2000 |

(Continued)

OTHER PUBLICATIONS

US 8,398,630 B2, 03/2013, Demarais et al. (withdrawn)

(Continued)

*Primary Examiner* — Jaymi E Della
*Assistant Examiner* — Sean W Collins

(57) ABSTRACT

Systems for nerve and tissue modulation are disclosed. An example system may include an intravascular nerve modulation system including an elongated shaft having a proximal end region and a distal end region. The system may further include a bar element extending distally from the distal end region of the elongated shaft and one or more ablation transducers affixed to the bar element.

15 Claims, 6 Drawing Sheets

(56) References Cited

U.S. PATENT DOCUMENTS

| | | |
|---|---|---|
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,471,988 A * | 12/1995 | Fujio ................. A61B 8/12 600/439 |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |

(56) References Cited

U.S. PATENT DOCUMENTS

| | | |
|---|---|---|
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,931,805 A * | 8/1999 | Brisken ............ A61B 17/22012 604/22 |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |

(56) References Cited

U.S. PATENT DOCUMENTS

| | | |
|---|---|---|
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |

(56) References Cited

U.S. PATENT DOCUMENTS

| | | |
|---|---|---|
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |

(56) References Cited

U.S. PATENT DOCUMENTS

| | | |
|---|---|---|
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |

(56) References Cited

U.S. PATENT DOCUMENTS

| | | |
|---|---|---|
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |

(56) References Cited

U.S. PATENT DOCUMENTS

| | | |
|---|---|---|
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0004439 A1* | 1/2003 | Pant ............. A61B 17/2202 601/2 |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0039311 A1* | 2/2004 | Nita ............. A61B 17/22012 601/2 |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |

(56) References Cited

U.S. PATENT DOCUMENTS

| | | |
|---|---|---|
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0240231 A1 | 10/2005 | Aldrich et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0013269 A1* | 1/2007 | Huang ............ B06B 1/0292 310/334 |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |

(56) References Cited

U.S. PATENT DOCUMENTS

| | | |
|---|---|---|
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0093726 A1* | 4/2009 | Takayama ............... A61B 8/12 600/466 |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0246332 A1* | 9/2010 | Huang ..................... A61B 8/06 367/181 |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |

(56) References Cited

U.S. PATENT DOCUMENTS

| | | |
|---|---|---|
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0215106 A1* | 8/2012 | Sverdlik .......... A61B 17/22012 600/439 |
| 2012/0232326 A1 | 9/2012 | Habib |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2006105121 A2 | 10/2006 |
| WO | 2008014465 A2 | 1/2008 |
| WO | 2008126070 A2 | 10/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

Van Den Berg, "Light echoes image the human body," OLE, Oct. 2001, p. 35-37.

"IntraLuminal: Products," IntraLuminal Therapeutics, Inc., 2003, p. 1-9.

"Laser Catheter to Aid Coronary Surgery," TechTalk: MIT, Jan. 9, 1991, p. 1-4.

"Optical Coherence Tomography: Advantages of OCT," LightLab Imaging Technology.

"Optical Coherence Tomography: Image Gallery Cardiovascular Procedures," LightLab Imaging Technology.

"Optical Coherence Tomography: LightLab Imaging Starts US Cardiology Clinical Investigations," LightLab Imaging Technology, 2002.

(56) References Cited

OTHER PUBLICATIONS

"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.

Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.

(56) References Cited

OTHER PUBLICATIONS

Giliatt et al., "The Cause of Nerve Damage in Acute Compression," Trans Am Neurol Assoc, 1974: 99; 71-4.

Omura et al., "A Mild Acute Compression Induces Neurapraxia in Rat Sciatic Nerve," The International Journal of Neuroscience, vol. 114 (12), pp. 1561-1572.

Baun, "Interaction with Soft Tissue," Principles of General & Vascular Sonography, Chapter 2, pp. 23-24, Before Mar. 2012.

Blue Cross Blue Shield Medicaly Policy, "Surgery Section—MRI-Guided Focused Ultrasound (MRgFUS) for the Treatment of Uterine Fibroids and Other Tumors," 2005, 5 pages.

Gentry et al., "Combines 3D Intracardiac Echo and Ultrasound Ablation," Medical Imaging 2003: Ultrasonic and Signal Processing, vol. 5035, 2003, pp. 166-173.

Lafon et al., "Optmizing the Shape of Ultrasound Transducers for Interstitial Thermal Ablations," MEd Phys. Mar. 2002; 29(3): 290-7 (abstract only).

G. Ter Haar, "Ultrasound Focal Beam Surgery," Ultrasound in Med. & Biol., 1995, vol. 21, No. 9, pp. 1089-1100.

Seip et al., "Transurethral High Intensity Focused Ultrasound: Catheter Based Prototypes and Experimental Results," IEEE Ultrasonics Symposium Proceeding, 2000, 4 pages.

Toytman et al., "Tissue Dissection with Ultrafast Laser Using Extended and Multiple Foci," SPIE Proceeding, Optical Interactions with Tissues and Cells XXI, vol. 7562, 2010, 10 pages.

Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.

Andrew Eastman et al, "Thrust measurements and flow field analysis of a piezoelectrically actuated oscillating cantilever", Experiments in Fluids ; Experimental Methods and Their Applications to Fluid Flow, Springer, Berlin, DE, (Sep. 5, 2012), vol. 53, No. 5, doi:10.1007/S00348-012-1373-6, ISSN 1432-1114, pp. 1533-1543, XP035133497 [A] 1-15.

* cited by examiner

SELF-COOLING ULTRASOUND ABLATION CATHETER

CROSS-REFERENCE TO RELATED APPLICATIONS

This application claims priority under 35 U.S.C. § 119 to U.S. Provisional Ser. No. 61/704,205, filed Sep. 21, 2012, the entirety of which is incorporated herein by reference.

TECHNICAL FIELD

The present disclosure relates generally to methods and apparatuses for nerve modulation techniques such as ablation of nerve tissue or other modulation techniques through the walls of blood vessels.

BACKGROUND

Certain treatments may require the temporary or permanent interruption or modification of select nerve function. One example treatment is renal nerve ablation, which is sometimes used to treat conditions related to congestive heart failure or hypertension. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many nerves (and nervous tissue such as brain tissue), including renal nerves, run along the walls of or in close proximity to blood vessels and thus can be accessed intravascularly through the walls of the blood vessels. In some instances, it may be desirable to ablate perivascular nerves using ultrasonic energy. In other instances, the perivascular nerves may be ablated by other means including application of thermal, radiofrequency, laser, microwave, and other related energy sources to the target region. Ultrasound transducers may dissipate some energy as heat into the blood and surrounding tissue as well as causing the ultrasound transducers to become hot. This may result in blood damage, clotting, and/or protein fouling of the transducer among other undesirable side effects. In some instances, overheating of the ultrasound transducer may result in the failure of the transducers. It may be desirable to provide for alternative systems and methods for intravascular nerve modulation with increased cooling of the transducers.

SUMMARY

This disclosure is directed to several alternative designs, materials and methods of manufacturing medical device structures and assemblies for performing nerve ablation.

Accordingly, one illustrative embodiment is a system for intravascular nerve modulation system that may include an elongated shaft having a proximal end region and a distal end region. A bar element configured to vibrate at a low frequency may extend distally from the distal end region of the elongated shaft. A proximal end of the bar element may be attached to the distal end of the elongated shaft such that the distal end of the bar element is free to vibrate. When subjected to a first frequency, the bar element may vibrate. One or more ablation transducers configured to operate at a second frequency may be affixed to the bar element. Another illustrative embodiment is an intravascular nerve modulation system that may include a catheter shaft having a proximal end region, a distal end region, and a lumen extending therebetween. The system may further include an elongated shaft disposed within the lumen of the catheter shaft and having a proximal end region and a distal end region. A driver may be connected to the proximal end region of the elongated shaft. One or more ablation transducers may be secured to a distal end region of the elongated shaft.

Another illustrative embodiment is an intravascular nerve modulation system that may include a catheter shaft having a proximal end region, a distal end region, and a lumen extending therebetween. The modulation system may further include a bar element and a tension member positioned adjacent to the distal end region of the catheter shaft. One or more ablation transducers may be secured to a distal end region of the bar element. The bar element may be connected to a control unit.

The above summary of an example embodiment is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
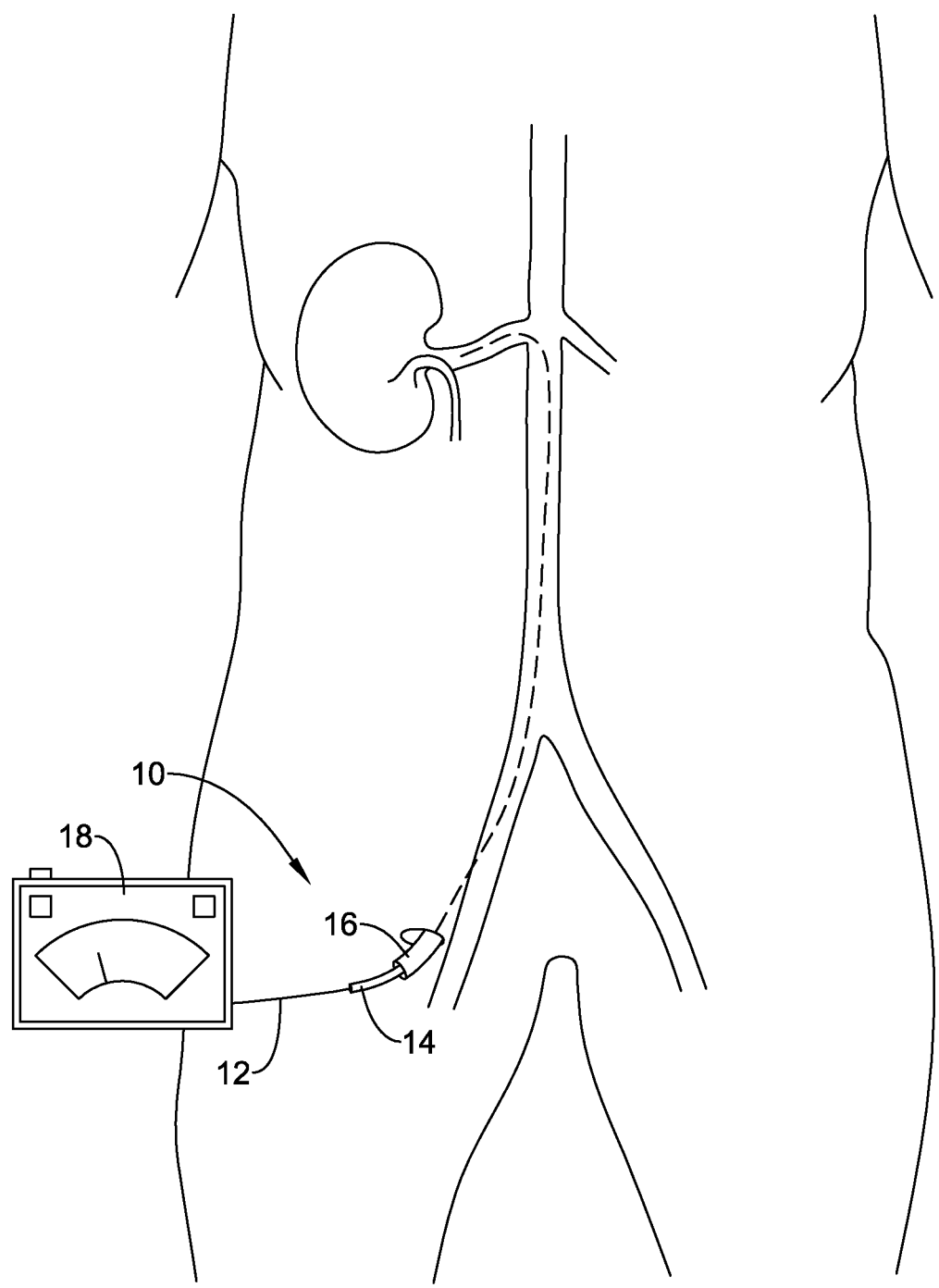
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions ranges and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

Certain treatments require the temporary or permanent interruption or modification of select nerve function. One example treatment is renal nerve ablation, which is sometimes used to treat conditions related to congestive heart failure or hypertension. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

While the devices and methods described herein are discussed relative to renal nerve modulation, it is contemplated that the devices and methods may be used in other locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, tumor ablation, benign prostatic hyperplasia therapy, nerve excitation or blocking or ablation, modulation of muscle activity, hyperthermia or other warming of tissues, etc. In some instances, it may be desirable to ablate perivascular renal nerves with ultrasound ablation.

Ultrasound energy may be used to generate heat at a target location. The high frequency sound waves produced by an ultrasonic transducer may be directed at a target region and absorbed at the target region. As the energy emitted is absorbed, the temperature of the target region may rise. In order to perform renal nerve ablation, target nerves must be heated sufficiently to make them nonfunctional, while thermal injury to the artery wall is undesirable. Heating of the artery wall may also increase pain during the procedure, which is also undesirable. When a portion of tissue is ablated, tissue properties change and increased attenuation of the ultrasound energy can make ablation past this ablated tissue difficult. Ultrasound ablation catheters may also generate significant heat in the ultrasound transducers may cause clots to form on the transducers, damage to the blood, or damage to the transducers among other undesirable side effects. As the ablation transducers heat, the energy conversion efficiency of those devices is lowered, thus generating more heat. Thus, normal operations of ablation transducers may be characterized by increasingly lower efficiency during operation. The efficiency of the ablation transducers may be enhanced using a cooling mechanism. One possible cooling mechanism is increasing the flow of blood past the transducers, providing passive cooling to the ablation transducers. In some instances, this may be accomplished by moving the ablation transducers back and forth in the blood thus increasing heat transfer to the blood and mixing of the blood. This may facilitate cooling of the transducers and/or reduce build-up of clots or other proteins.

FIG. 1 is a schematic view of an illustrative renal nerve modulation system 10 in situ. System 10 may include an element 12 for providing power to a transducer disposed adjacent to, about, and/or within a central elongated shaft 14 and, optionally, within a sheath 16, the details of which can be better seen in subsequent figures. A proximal end of element 12 may be connected to a control and power element 18, which supplies the necessary electrical energy to activate the one or more transducers at or near a distal end of the element 12. The control and power element 18 may include monitoring elements to monitor parameters such as power, temperature, voltage, pulse duration and/or frequency and other suitable parameters as well as suitable controls for performing the desired procedure. In some instances, the power element 18 may control an ultrasound ablation transducer. The ablation transducer may be configured to operate at a frequency of about 9-10 megahertz (MHz). It is contemplated that any desired frequency may be used, for example, from 1-20 MHz. In addition, it is contemplated that frequencies outside this range may also be used, as desired. While the term "ultrasound" is used herein, this is not meant to limit the range of vibration frequencies contemplated. For example, it is contemplated that the perivascular nerves may be ablated by other means including application of thermal, radiofrequency, laser, microwave, and other related energy sources to the target region.

Figure 2:
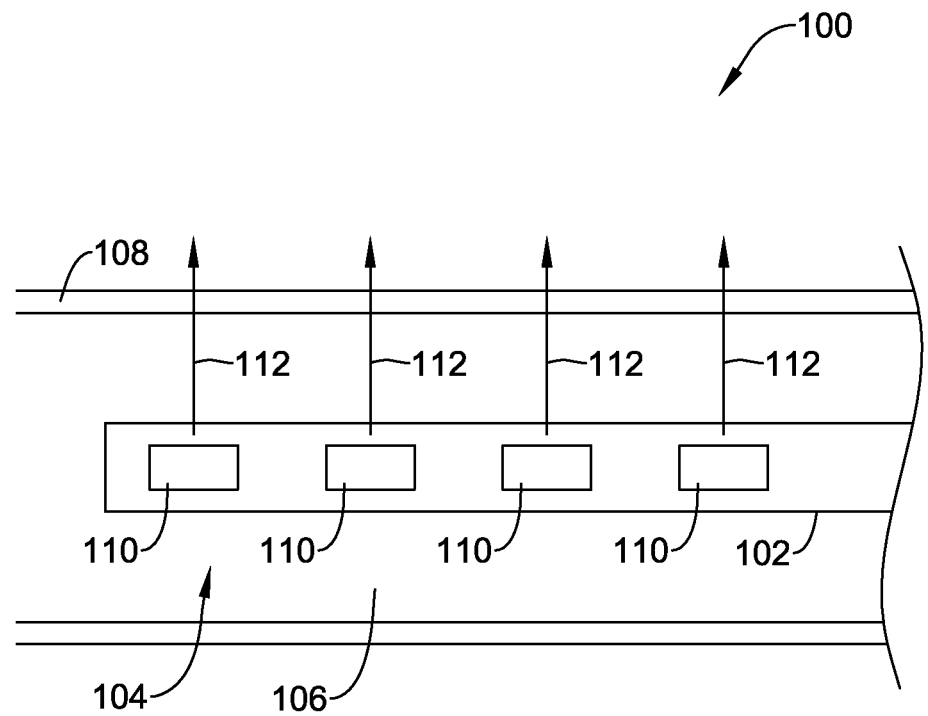
FIG. 2 illustrates a portion of an example intravascular nerve modulation system.

FIG. 2 is an illustrative embodiment of a distal end of a renal nerve modulation system 100 disposed within a body lumen 106 having a vessel wall 108. The vessel wall 108 may be surrounded by local body tissue. The local body tissue may comprise adventitia and connective tissues, nerves, fat, fluid, etc. in addition to the muscular vessel wall 108. The system 100 may include an elongate shaft 102 having a distal end region 104. The elongate shaft 102 may extend proximally from the distal end region 104 to a proximal end configured to remain outside of a patient's body. The proximal end of the elongate shaft 102 may include a hub attached thereto for connecting other treatment devices or providing a port for facilitating other treatments. It is contemplated that the stiffness of the elongate shaft 102 may be modified to form a modulation system 100 for use in various vessel diameters and various locations within the vascular tree. The elongate shaft 102 may further include one or more lumens extending therethrough. For example, the elongate shaft 102 may include a guidewire lumen and/or one or more auxiliary lumens. The lumens may be configured in any way known in the art. For example, the guidewire lumen may extend the entire length of the elongate shaft 102 such as in an over-the-wire catheter or may extend only along a distal portion of the elongate shaft 102 such as in a single operator exchange (SOE) catheter. These examples are not intended to be limiting, but rather examples of some possible configurations. While not explicitly shown, the modulation system 100 may further include temperature sensors/wire, an infusion lumen, radiopaque marker bands, fixed guidewire tip, a guidewire lumen, external sheath, centering basket, and/or other components to facilitate the use and advancement of the system 100 within the vasculature.

The system 100 may include an array of ultrasound ablation transducers 110 positioned adjacent the distal end region 104 of the elongate shaft. However, the transducer array 110 may be placed at any longitudinal location along the elongate shaft 102 desired. It is contemplated that the array may include any number of transducers 110 desired. It is further contemplated that more than one row of transducers 110 may be disposed on the elongate shaft 102. In some instances, the ablation transducers 110 may include a number of transducers (two, three, four, or more) spaced about the circumference of the elongate shaft 102. This may allow for ablation of multiple circumferential locations about the body lumen simultaneously. In other embodiments, the transducers 110 may comprise a focused or phased array of transducers. The array may be configured to be directed at a focus region such that multiple transducers are radiating energy at a common target region. It is further contemplated that the ablation transducers 110 may comprise a plurality of longitudinally spaced transducers.

The ablation transducers 110 may be formed from any suitable material such as, but not limited to, lead zirconate titanate (PZT). It is contemplated that other ceramic or piezoelectric materials may also be used. While not explicitly shown, the ablation transducers 110 may have a first radiating surface, a second radiating surface, and a perimeter surface extending around the outer edge of the ablation transducer 110. In some instances, the transducers 110 may include a layer of gold, or other conductive layer, disposed on the first and/or second side over the PZT crystal for connecting electrical leads to the transducers 110. In some embodiments, the ablation transducers 110 may be structured to radiate acoustic energy from a single radiating surface. In such an instance, one radiating surface may include a backing layer to direct the acoustic energy in a single direction. In other embodiments, the ablation transducers 110 may be structured to radiate acoustic energy from two radiating surfaces. In some instances, one or more tie layers may be used to bond the gold to the PZT. For example, a layer of chrome may be disposed between the PZT and the gold to improve adhesion. In other instances, the transducers 110 may include a layer of chrome over the PZT followed by a layer of nickel, and finally a layer of gold. These are just examples. It is contemplated that the layers may be deposited on the PZT using sputter coating, although other deposition techniques may be used as desired. While the ablation transducers 110 are described as ultrasonic transducers, it is contemplated that other methods and devices for raising the temperature of the nerves may be used, such as, but not limited to: radiofrequency, microwave, or other acoustic, optical, electrical current, direct contact heating, or other heating.

It is contemplated that the radiating surface (surface which radiates acoustic energy) of the transducers 110 may take any shape desired, such as, but not limited to, square, rectangular, polygonal, circular, oblong, etc. The acoustic energy from the radiating surface of the transducers 110 may be transmitted in a spatial pressure distribution related to the shape of the transducers 110. With exposures of appropriate power and duration, lesions formed during ablation may take a shape similar to the contours of the pressure distribution. As used herein, a "lesion" may be a change in tissue structure or function due to injury (e.g. tissue damage caused by the ultrasound). Thus, the shape and dimensions of the transducers 110 may be selected based on the desired treatment and the shape best suited for that treatment. It is contemplated that the transducers 110 may also be sized according to the desired treatment region. For example, in renal applications, the transducers 110 may be sized to be compatible with a 6 French guide catheter, although this is not required.

In some embodiments, the transducers 110 may be formed of a separate structure and attached to the elongate shaft 102. For example, the transducers 110 may be bonded or otherwise attached to the elongate shaft 102. In some instances, the transducers 110 may include a ring or other retaining or holding mechanism (not explicitly shown) disposed around the perimeter of the transducers 110 to facilitate attachment of the transducers 110. The transducers 110 may further include a post, or other like mechanism, affixed to the ring such that the post may be attached to the elongate shaft 102 or other member. In some instances, the rings may be attached to the transducers 110 with a flexible adhesive, such as, but not limited to, silicone. However, it is contemplated that the rings may be attached to the transducers 110 in any manner desired. While not explicitly shown, in some instances, the elongate shaft 102 may be formed with grooves or recesses in an outer surface thereof. The recesses may be sized and shaped to receive the transducers 110. For example, the ablation transducers 110 may be disposed within the recess such that a first surface contacts the outer surface of the elongate shaft 102 and a second surface is directed towards a desired treatment region. However, it is contemplated that the transducers 110 may be affixed to the elongate shaft in any manner desired.

In some embodiments, the transducers 110 may be affixed to an outer surface of the elongate shaft 102 such that the surfaces of the transducers 110 are exposed to blood flow through the vessel. As the power is relayed to the ablation transducers 110, the power that does not go into generating acoustic power generates heat. As the ablation transducers 110 heat, they become less efficient, thus generating more heat. Passive cooling provided by the flow of blood may help improve the efficiency of the transducers 110. However, in some instances, additional cooling may be provided by introducing a cooling fluid or other cooling mechanism to the modulation system 100.

While not explicitly shown, the ablation transducers 110 may be connected to a control unit (such as control unit 18 in FIG. 1) by electrical conductor(s). In some embodiments, the electrical conductor(s) may be disposed within a lumen of the elongate shaft 102. In other embodiments, the electrical conductor(s) may extend along an outside surface of the elongate shaft 102. The electrical conductor(s) may provide electricity to the transducers 110 which may then be converted into acoustic energy. The acoustic energy may be directed from the transducers 110 in a direction generally perpendicular to the radiating surfaces of the transducers 110, as illustrated at lines 112. As discussed above, acoustic energy radiates from the transducers 110 in a pattern related to the shape of the transducers 110 and lesions formed during ablation take shape similar to contours of the pressure distribution.

Figure 3:
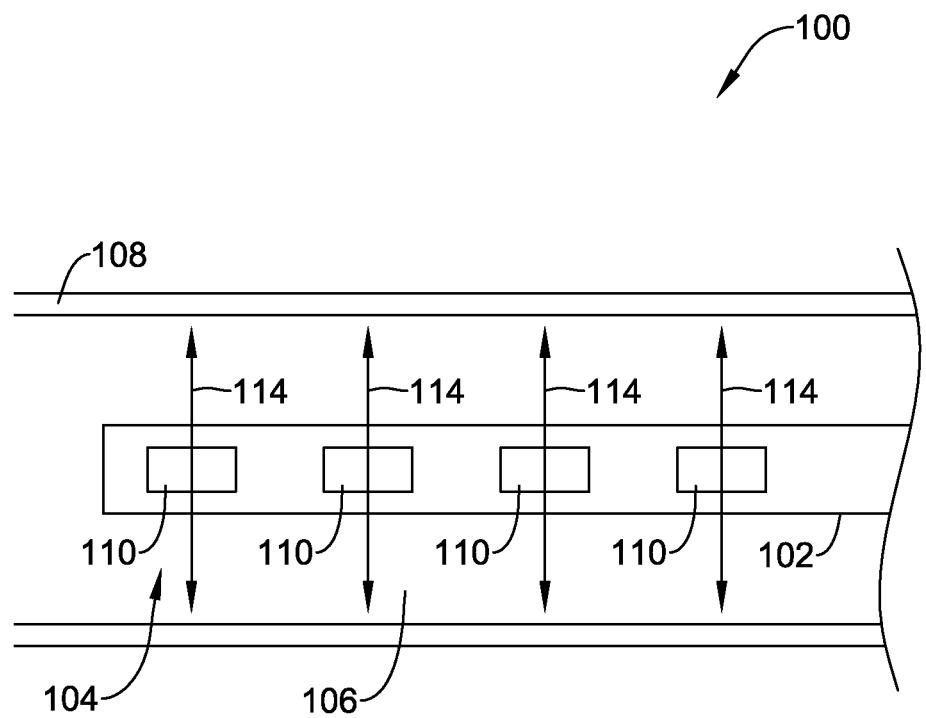
FIG. 3 illustrates a portion of another example intravascular nerve modulation system.

It is contemplated that the modulation system 100 may be configured to operate in an ablation mode and a low frequency mode. In the low frequency mode, the system 100 may be operated at a first, lower frequency with a higher amplitude. It is contemplated that the low frequency may range from about 10 KHz to 200 KHz. It is further contemplated that the first frequency may include various other frequency ranges, as desired, based upon the physical affects produced. This may allow the distal end region 104 of the elongate shaft 102 to shake, vibrate, or otherwise move back and forth as shown by arrows 114 in FIG. 3. The directional arrows 114 are merely exemplary and are not intended to limit the movement of the elongate shaft 102 to any specific direction. It is contemplated that while the vibrations may cause the elongate shaft 102 to move in a direction generally orthogonal to the longitudinal axis of the elongate shaft 102, this is not required. The movement may provide additional convective cooling to the transducers 110. Additionally, the low frequency mode may also allow blood to accelerate, thus increasing convection for improved heat transfer to cool the transducers 110. A cooler transducer 110 may cause less direct thermal injury to the artery wall and to the blood, with less clotting and debris build-up on the transducer 110 and less debris embolization. In the ablation mode, the system 100 may be operated at a second, higher frequency, with low displacement amplitude. The second frequency may range from about 9-10 megahertz (MHz). It is contemplated that any desired frequency may be used, for example, from 1-20 MHz beyond. In the ablation mode, acoustic energy 112 may be directed from the transducers 110 to form lesions in the desired target region. In general, the second frequency may be higher than the first frequency. The reverse configuration may also be utilized.

Once the modulation system 100 has been advanced to the treatment region, energy may be supplied to the ablation transducers 110. In some instances, the transducers 110 may function as both the high frequency and low frequency transducers and may be alternately activated in a high frequency ablation mode and a low frequency "shaking" mode. In other embodiments, separate transducers may be supplied that are tuned to different frequencies. For example, while not explicitly shown, a first set of transducers may be tuned to be excitable at a high frequency to perform tissue modulation and/or ablation and a second set of transducers may be tuned to be excitable at a low frequency to perform intermittent shaking. It is contemplated that the high frequency transducers and the low frequency transducers may be operated in an alternating manner or simultaneously, as desired. It is further contemplated that the transducers 110 may be placed at various angles to improve the effectiveness of convective cooling. Additionally, the elongate shaft 102 may include structure or features, such as vanes, to improve the effectiveness of convective cooling.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide sheath such as the sheath 16 shown in FIG. 1. Once the ablation transducers 110 of the modulation system 100 have been placed adjacent to the desired treatment area, positioning mechanisms may be deployed, if so provided. While not explicitly shown, the ablation transducers 110 may be connected to a single control unit or to separate control units (such as control unit 18 in FIG. 1) by electrical conductors. As discussed above, the ablation transducers 110 may be connected to one or more control units, which may drive and/or monitor the system 100 with one or more parameters such as, but not limited to, frequency for performing the desired ablation procedure. In some embodiments, the control unit may include an oscillator. More specifically, the oscillator may have a predetermined range of frequencies such as the first frequency and the second frequency (as previously discussed). Exemplary oscillators may include a mechanical oscillator, acoustic oscillator, or other suitable oscillators known to those skilled in the art. Those skilled in the art, however, will appreciate that any other suitable control unit and/or energy source may also be contemplated.

Once the modulation system 100 has been advanced to the treatment region, energy may be supplied to the ablation transducers 110. As discussed above, the energy may be supplied to both the ablation transducers 110 and the shaking transducers, if so provided, simultaneously or in an alternating fashion as desired or the transducers 110 may be alternately activated at a high frequency and a low frequency. The amount of energy delivered to the ablation transducers 110 may be determined by the desired treatment as well as the feedback provided by monitoring systems.

In some instances, the elongate shaft 102 may be rotated and additional ablation can be performed at multiple locations around the circumference of the vessel 106. In some instances, a slow automated "rotisserie" rotation can be used to work around the circumference of the vessel 106, or a faster spinning can be used to simultaneously ablate around the entire circumference. The spinning can be accomplished with a distal micro-motor or by spinning a drive shaft from the proximal end. In some embodiments, ultrasound sensor information can be used to selectively turn on and off the ablation transducers to warm any cool spots or accommodate for veins, or other tissue variations. The number of times the elongate shaft 102 is rotated at a given longitudinal location may be determined by the number and size of the ablation transducers 110 on the elongate shaft 102. Once a particular location has been ablated, it may be desirable to perform further ablation procedures at different longitudinal locations. Once the elongate shaft 102 has been longitudinally repositioned, energy may once again be delivered to the ablation transducers 110. If necessary, the elongate shaft 102 may be rotated to perform ablation around the circumference of the vessel 106 at each longitudinal location. This process may be repeated at any number of longitudinal locations desired. It is contemplated that in some embodiments, the system 100 may include transducer arrays 110 at various positions along the length of the modulation system 100 such that a larger region may be treated without longitudinal displacement of the elongate shaft 102.

Figure 4:
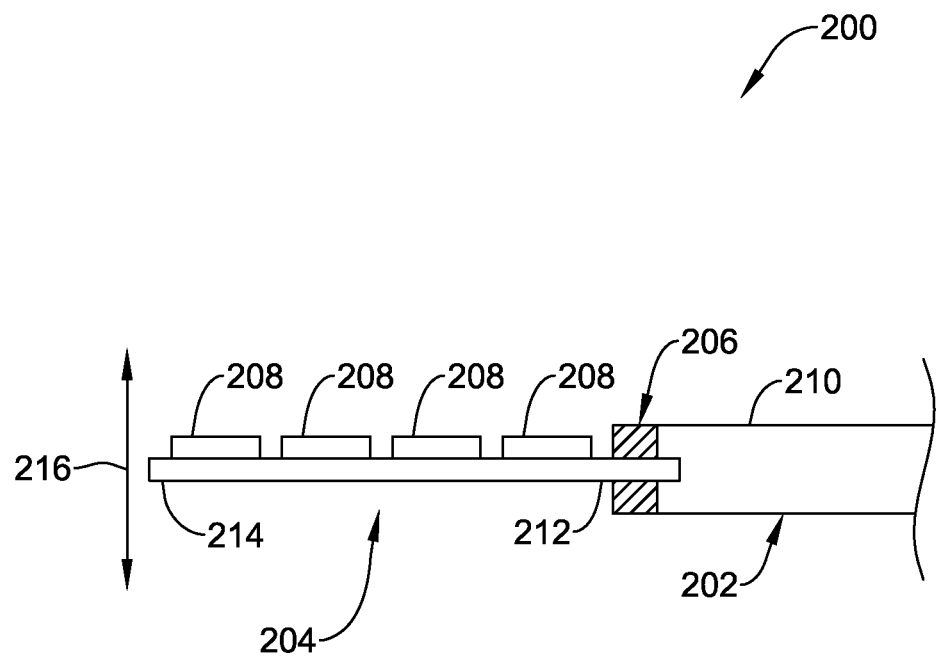
FIG. 4 illustrates a portion of another example intravascular nerve modulation system.

FIG. 4 is a schematic view of a distal end of an illustrative intravascular nerve modulation system 200. While not explicitly shown, the nerve modulation system 200 may be configured to be advanced within a body lumen having a vessel wall. The vessel wall may be surrounded by local body tissue. The local body tissue may comprise adventitia and connective tissues, nerves, fat, fluid, etc. in addition to the muscular vessel wall. A portion of the surrounding tissue may be the desired treatment region. As shown, the system 200 may include an elongated shaft 202 having a distal end region 210. The elongated shaft 202 may extend proximally from the distal end region 210 to a proximal end region (not shown) configured to remain outside of a patient's body. The proximal end of the elongated shaft 202 may include a hub attached thereto for connecting other diagnostic and/or treatment devices for providing a port for facilitating other interventions.

The elongated shaft 202 may have a long, thin, flexible tubular configuration. A person skilled in the art will appreciate that other suitable configurations such as, but not limited to, rectangular, oval, irregular, or the like may also be contemplated. In addition, the elongated shaft 202 may have a cross-sectional configuration adapted to be received in a desired vessel, such as a renal artery. For instance, the elongated shaft 202 may be specially sized and configured to accommodate passage through the intravascular path, which leads from a percutaneous access site in, for example, the femoral, brachial, or radial artery, to a targeted treatment site, for example, within a renal artery.

It is contemplated that the stiffness of the elongated shaft 202 may be modified to form modulation system 200 for use in various vessel diameters. To this end, the material used for manufacturing the elongated shaft 202 may include any suitable biocompatible material such as, but are not limited to, polymers, metals, alloys, either in combination or alone. The material employed may have enough stiffness for use in various lumen diameters, and sufficient flexibility to maneuver through tortuous and/or stenotic lumens, avoiding any undesirable tissue injuries.

The elongated shaft 202 may further include one or more lumens (not explicitly shown) extending therethrough. For example, the elongated shaft 202 may include a guidewire lumen and/or one or more auxiliary lumens. The lumens may have a variety of configurations and/or arrangements. For example, the guidewire lumen may extend the entire length of the elongated shaft 202 such as in an over-the-wire catheter or may extend only along a distal portion of the elongated shaft 202 such as in a single operator exchange (SOE) catheter. These examples are not intended to be limiting, but rather examples of some optional configurations. While not explicitly shown, the modulation system 200 may further include temperature sensor/wire, an infusion lumen, radiopaque marker bands, fixed guidewire tip, a guidewire lumen, external sheath, and/or other components to facilitate the use and advancement of the system 200 within the vasculature. It is further contemplated that the modulation system 200 may include one or more centering baskets, expandable framework, and/or expandable balloons to center or otherwise position the modulation system 200 within the body lumen.

The system 200 may further include a bar element 204 having a proximal end region 212 and a distal end region 214. In some embodiments, the bar element 204 may include a long, thin bar-shaped transducer disposed adjacent the distal end region 210 of the elongate shaft 202. It may be contemplated that other suitable shapes such as, but limited to rectangular, square, cylindrical, oval, irregular, and so forth may be used, as desired. In some instances, the bar element 204 may be attached to the distal end region of the elongated shaft 202 such that the proximal end region 212 is physically constrained. The distal end region 214 of the bar element may be unconstrained.

In some embodiments, the bar element 204 may be may be formed from any suitable material such as, but not limited to, lead zirconate titanate (PZT). It is contemplated that other ceramic or piezoelectric materials, such as, but not limited to barium titanate, may also be used. In some instances, the bar element 204 may include a layer of gold, or other conductive layer, disposed on a first and/or second side surface over the PZT crystal for connecting electrical leads to the bar element 204. In some instances, one or more tie layers may be used to bond the gold to the PZT. For example, a layer of chrome may be disposed between the PZT and the gold to improve adhesion. In other instances, the bar element 204 may include a layer of chrome over the PZT followed by a layer of nickel, and finally a layer of gold. These are just examples. It is contemplated that the layers may be deposited on the PZT using sputter coating, although other deposition techniques may be used as desired.

In some embodiments, the proximal end region 212 of the bar element 204 may connected to the distal end region 210 of the elongated shaft 202 via a connecting member 206. Exemplary connecting members 206 may include structures such as, but not limited to, male-female connections, friction-fit, threading, luer-connections, clamping mechanisms, and so forth. In one embodiment, the connecting member 206 may include a clamp (not explicitly shown), which may be fixedly secured to the distal end region 210 of the elongated shaft at a proximal end and coupled to the proximal end region 212 of the bar element 204 at a distal end thereof. In some embodiments, the bar element 204 may include a ring or other retaining or holding mechanism (not explicitly shown) disposed around the perimeter of the bar element 204 to facilitate attachment of the bar element 204. The bar element 204 may further include a post, or similar mechanism, affixed to the ring such that the post may be attached to the elongated shaft 202 or other member. Those skilled in the art will appreciate that various other suitable connection mechanisms may be used couple the bar element 204 to the distal end region 210 of the elongated shaft 202. Alternatively, the bar element 204 may be formed of a separate structure and may be directly attached to the distal end region 210 of the elongated shaft 202. While the proximal end region 212 of the bar element 204 may be attached to the distal end region 210, the distal end region 214 of the bar element 204 may remain free, or unconstrained, forming a cantilever extending distally from the end region 210.

The system 200 may further include one or more ablation transducers 208 mounted on the bar element 204. While the Figure illustrates four ablation transducers 208, it is contemplated that the modulation system 200 may include any number of ablation transducers desired, such as, but not limited to, one, two, three, or more. In some instances, the ablation transducers 208 may include a number of transducers (two, three, four, or more) spaced about the circumference of the bar element 204. This may allow for ablation of multiple circumferential locations about the body lumen simultaneously. In other embodiments, the ablation transducers 208 may comprise a focused or phased array of transducers. The array may be configured to be directed at a focus region such that multiple transducers are radiating energy at a common target region. It is further contemplated that the ablation transducers 208 may comprise a plurality of longitudinally spaced transducers.

While the ablation transducers 208 are described as ultrasonic transducers, it is contemplated that other methods and devices for raising the temperature of the nerves may be used, such as, but not limited to: radiofrequency, microwave, or other acoustic, optical, electrical current, direct contact heating, or other heating. The same may also be true of bar element 204. The ablation transducers 208 may be formed from any suitable material such as, but not limited to, lead zirconate titanate (PZT). It is contemplated that other ceramic or piezoelectric materials may also be used. While not explicitly shown, the ablation transducers 208 may have a first radiating surface, a second radiating surface, and a perimeter surface extending around the outer edge of the ablation transducers 208. In some instances, the ablation transducers 208 may include a layer of gold, or other conductive layer, disposed on the first and/or second side over the PZT crystal for connecting electrical leads to the ablation transducers 208. In some embodiments, the ablation transducers 208 may be structured to radiate acoustic energy from a single radiating surface. In such an instance, one radiating surface may include a backing layer to direct the acoustic energy in a single direction. In other embodiments, the ablation transducers 208 may be structured to radiate acoustic energy from two radiating surfaces. In some instances, one or more tie layers may be used to bond the gold to the PZT. For example, a layer of chrome may be disposed between the PZT and the gold to improve adhesion. In other instances, the transducers 208 may include a layer of chrome over the PZT followed by a layer of nickel, and finally a layer of gold. These are just examples. It is contemplated that the layers may be deposited on the PZT using sputter coating, although other deposition techniques may be used as desired.

It is contemplated that the radiating surface (surface which radiates acoustic energy) of the ablation transducers 208 may take any shape desired, such as, but not limited to, square, rectangular, polygonal, circular, oblong, etc. The acoustic energy from the radiating surface of the ablation transducers 208 may be transmitted in a spatial pressure distribution related to the shape of the ablation transducers 208. With exposures of appropriate power and duration, lesions formed during ablation may take a shape similar to the contours of the pressure distribution. As used herein, a "lesion" may be a change in tissue structure or function due to injury (e.g. tissue damage caused by the ultrasound). Thus, the shape and dimensions of the ablation transducers 208 may be selected based on the desired treatment and the shape best suited for that treatment. It is contemplated that the ablation transducers 208 may also be sized according to the desired treatment region. For example, in renal applications, the ablation transducers 208 may be sized to be compatible with a 6 French guide catheter, although this is not required.

In some embodiments, the ablation transducers 208 may be formed of a separate structure and attached to the bar element 204. For example, the ablation transducers 208 may be bonded or otherwise attached to the bar element 204. In some instances, the ablation transducers 208 may include a ring or other retaining or holding mechanism (not explicitly shown) disposed around the perimeter of the ablation transducers 208 to facilitate attachment of the ablation transducers 208. The ablation transducers 208 may further include a post, or other like mechanism, affixed to the ring such that the post may be attached to the bar element 204 or other member. In some instances, the rings may be attached to the ablation transducers 208 with a flexible adhesive, such as, but not limited to, silicone. However, it is contemplated that the rings may be attached to the ablation transducers 208 in any manner desired. While not explicitly shown, in some instances, the bar element 204 may be formed with grooves or recesses in an outer surface thereof. The recesses may be sized and shaped to receive the ablation transducers 208. For example, the ablation transducers 208 may be disposed within the recess such that a first radiating surface contacts the outer surface of the bar element 204 and a second radiating surface is directed towards a desired treatment region. However, it is contemplated that the ablation transducers 208 may be affixed to the bar element 204 in any manner desired. It is further contemplated that in some instances, the ablation transducers 208 may be affixed adjacent the distal end region 210 of the elongate shaft 202, or along any longitudinal length thereof, as desired.

The ablation transducers 208 may be connected to a control unit (such as control unit 18 in FIG. 1) by electrical conductor(s). In some embodiments, the electrical conductor(s) may be disposed within a lumen of the elongate shaft 202. In other embodiments, the electrical conductor(s) may extend along an outside surface of the elongate shaft 202. The electrical conductor(s) may provide electricity to the ablation transducers 208, which may then be converted into acoustic energy. The acoustic energy may be directed from the ablation transducers 208 in a direction generally perpendicular to the radiating surfaces of the ablation transducers 208. As discussed above, acoustic energy radiates from the ablation transducers 208 in a pattern related to the shape of the transducers 208 and lesions formed during ablation take shape similar to contours of the pressure distribution.

The bar element 204 may also be connected to a control unit (such as control unit 18 in FIG. 1) by electrical conductor(s). In some embodiments, the electrical conductor(s) may be disposed within a lumen of the elongate shaft 202. In other embodiments, the electrical conductor(s) may extend along an outside surface of the elongate shaft 202. The electrical conductor(s) may provide electricity to the bar element 204 which may then be converted into vibrational energy. The control unit may be configured to supply energy at a low frequency and at a higher amplitude relative to the frequency and amplitudes used for ablation to cause movement of the bar element 204. The vibrational energy may cause the bar element 204 to move back and forth in a direction 216 generally orthogonal to a longitudinal axis of the system 200. However, the bar element 204 may vibrate in any other suitable directions known to those skilled in the art. The cantilever system created by constraining the proximal end 212 of the bar element 204 may allow the distal end 214 of the bar element 204 to move more than the proximal end. The movement of the bar element 204 may move the ablation transducers 208 back and forth within blood flow in the vessel which may increase heat transfer from the transducers 208 to the blood, and thus cooling the ablation transducers 208. The movement of the bar element 204 may also increase mixing of the blood, as well as reducing build-up of clots and/or other proteins (e.g., along transducers 208).

The modulation system 200 may be configured to operate at a first frequency for causing physical movement of the bar element 204 and a second frequency for performing tissue modulation using the ablation transducers 208. Here, the first frequency may include a low frequency that may provide physical movement to the bar element 204, thus providing cooling to the ablation transducers 208, as discussed above. It is contemplated that the first frequency may range from about 10 KHz to 200 KHz. It is further contemplated that the first frequency may include various other frequency ranges, as desired, based upon the physical affects produced. The second frequency may include a high frequency, which may ablate the target tissue. The second frequency may range from about 9-10 megahertz (MHz). It is contemplated that any desired frequency may be used, for example, from 1-20 MHz beyond. In general, the second frequency may be higher than the first frequency. The reverse configuration may also be utilized.

In addition, while ablation transducers 208 are shown in FIG. 4 mounted on bar element 204, other arrangements are contemplated. For example, ablation transducers 208 may be attached to the outer surface of shaft 202 (e.g., adjacent to distal end region 210). In some of these embodiments, the outer surface of shaft 202 may include a vibrating surface or member (e.g., that may be configured to vibrate). In other embodiments, one or more of transducers 208 may be configured to vibrate when subjected to a first frequency (e.g., to help dissipate and/or reduce fouling of transducers 208) and one or more other transducers 208 may be configured to ablate tissue when subjected to a second frequency. In still other embodiments, one or more of transducers 208 may include a first portion that is configured to vibrate when subjected to a first frequency (e.g., to help dissipate and/or reduce fouling of transducers 208) and a second portion that is configured to ablate tissue when subjected to a second frequency. In still other embodiments, transducers 208 may be configured to vibrate when subjected a first frequency and to ablate when subjected to a second frequency. These are just examples.

As discussed above, the bar element 204 and the ablation transducers 208 may be connected to one or more control units, which may provide and/or monitor the system 200 with one or more parameters such as, but not limited to, frequency for performing the desired ablation procedure. In some embodiments, the control unit may include an oscillator. More specifically, the oscillator may have a predetermined range of frequencies such as the first frequency and the second frequency (as previously discussed). Exemplary oscillators may include a mechanical oscillator, acoustic oscillator, or other suitable oscillators known to those skilled in the art. Those skilled in the art, however, will appreciate that any other suitable control unit and/or energy source may also be contemplated.

The modulation system 200 may be advanced through the vasculature in any manner known in the art. For example, system 200 may include a guidewire lumen to allow the system 200 to be advanced over a previously located guidewire. In some embodiments, the modulation system 200 may be advanced, or partially advanced, within a guide sheath such as the sheath 16 shown in FIG. 1. Once the ablation transducers 208 of the modulation system 200 have been placed adjacent to the desired treatment area, positioning mechanisms may be deployed, such as centering baskets, if so provided. While not explicitly shown, the ablation transducers 208 and the bar element 204 may be connected to a single control unit or to separate control units (such as control unit 18 in FIG. 1) by electrical conductors.

Once the modulation system 200 has been advanced to the treatment region, energy may be supplied to the ablation transducers 208 and the bar element 204. In some instances, energy may first be supplied to the ablation transducers 208. As the energy is radiated from the ablation transducers 208, the ablation transducers 208 may begin to heat. The modulation system 200 may use temperature sensors, or the monitoring means, to monitor the temperature or efficiency of the ablation transducers 208. Once the ablation transducers 208 have reached a predetermined criteria, energy may then be supplied to the bar element 204. As discussed above, the energy supplied to the bar element 204 may result in physical movement of the bar element, and thus the ablation transducers 208. As the bar element 204 moves, increased convection may transfer heat away from the ablation transducers 208. It is contemplated that energy may be supplied to the ablation transducers 208 and the bar element 204 in an alternating fashion such that one is activated while the other is inactive. In other embodiments, the ablation transducers 208 and the bar element 204 may be activated simultaneously. The amount of energy delivered to the ablation transducers 208 may be determined by the desired treatment as well as the feedback provided by the system 200.

In some instances, the elongated shaft 202 may be rotated and additional ablation can be performed at multiple locations around the circumference of the vessel. In some instances, a slow automated "rotisserie" rotation can be used to work around the circumference of the vessel, or a faster spinning can be used to simultaneously ablate around the entire circumference. The spinning can be accomplished with a micro-motor or by spinning a drive shaft. In some embodiments, ultrasound sensor information can be used to selectively turn on and off the ablation transducers 208 to warm any cool spots or accommodate for veins, or other tissue variations. The number of times the elongated shaft 202 is rotated at a given longitudinal location may be determined by the number and size of the ablation transducers 208 on the bar element 204. Once a particular location has been ablated, it may be desirable to perform further ablation procedures at different longitudinal locations. Once the elongated shaft 202 has been longitudinally repositioned, energy may once again be delivered to the ablation transducers 208 and the bar element 204. If necessary, the elongated shaft 202 may be rotated to perform ablation around the circumference of the vessel at each longitudinal location. This process may be repeated at any number of longitudinal locations desired. It is contemplated that in some embodiments, the system 200 may include ablation transducers at various positions along the length of the modulation system 200 such that a larger region may be treated without longitudinal displacement of the elongated shaft 202.

Figure 5:
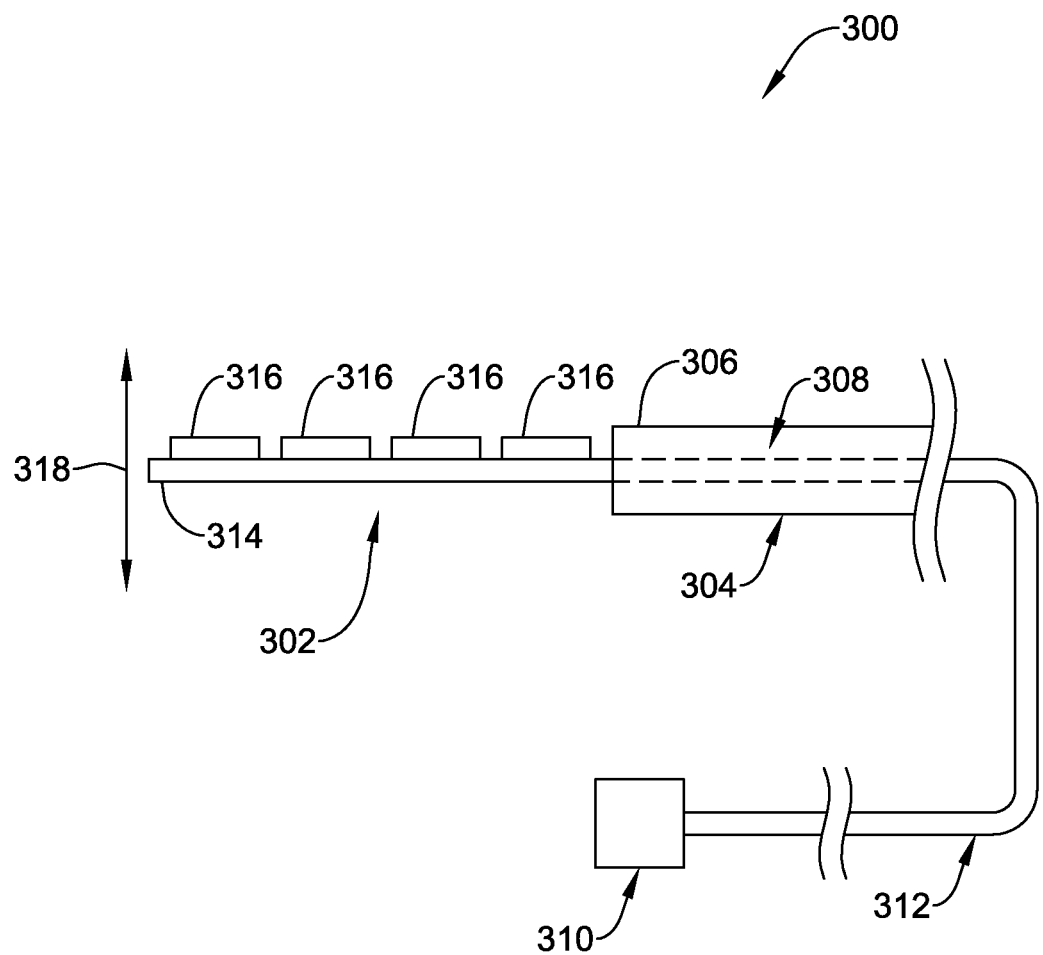
FIG. 5 illustrates a portion of another example intravascular nerve modulation system.

FIG. 5 is a schematic view of a distal end of another illustrative intravascular nerve modulation system 300 that may be similar in form and function to other systems disclosed herein. As shown, the modulation system 300 may include a catheter shaft 304 having a distal end region 306. The catheter shaft 304 may extend proximally to a point configured to remain outside of a patient's body. The proximal end of the catheter shaft 304 may include a hub attached thereto for connecting other treatment devices or providing a port for facilitating other treatments. It is contemplated that the stiffness of the catheter shaft 304 may be modified to form a modulation system 300 for use in various vessel diameters and various locations within the vascular tree. The catheter shaft 304 may include a lumen 308 extending between the proximal end region (not shown) and the distal end region 306

In addition, the catheter shaft 304 may have a cross-sectional configuration adapted to be received in a desired vessel, such as a renal artery. For instance, the catheter shaft 304 may specially be sized and configured to accommodate passage through the intravascular path, which leads from a percutaneous access site in, for example, the femoral, brachial, or radial artery, to a targeted treatment site, for example, within a renal artery. An exemplary embodiment may depict the catheter shaft 304 to take on a long, thin, flexible tube-shaped structure having a tubular cross-section; however, other contemplated cross-sections may include rectangular, irregular, or other suitable structures known to those skilled in the art.

The catheter shaft 304 may further include one or more lumens (not explicitly shown) in addition to lumen 308 extending therethrough. For example, the catheter shaft 304 may include a guidewire lumen and/or one or more auxiliary lumens. The lumens may be configured in any suitable way such as those ways commonly used for medical device. For example, the guidewire lumen may extend the entire length of the catheter shaft 304 such as in an over-the-wire catheter or may extend only along a distal portion of the catheter shaft 304 such as in a single operator exchange (SOE) catheter. These examples are not intended to be limiting, but rather examples of some possible configurations. While not explicitly shown, the modulation system 300 may further include temperature sensor/wire, an infusion lumen, radiopaque marker bands, fixed guidewire tip, a guidewire lumen, external sheath, and/or other components to facilitate the use and advancement of the system 300 within the vasculature.

The system 300 may further include an elongated shaft 302 having a proximal end region 312 and a distal end region 314. In one embodiment, the elongated shaft 302 may be disposed within the lumen 308 of the catheter shaft 304. For example, in some instances, the elongated shaft 302 and the catheter shaft 304 may be advanced through the vasculature together and the catheter shaft 304 retracted proximally to expose the elongated shaft 302 once the system 300 has been placed adjacent the desired treatment region. Alternatively, the elongated shaft 302 may be distally advanced out from the distal end of the catheter shaft 304. In other embodiments, the catheter shaft 304 may function as a guide catheter and may be advanced to the desired treatment region before the elongated shaft 302. In some embodiments, the elongated shaft 302 may have a tubular configuration. However, other suitable configuration such as rectangular, oval, irregular, or the like may also be contemplated. For example, the elongated shaft 302 may be a thin bar, wire, or other structure. The material employed to manufacture the elongated shaft 302 may include a suitable biocompatible material such as, but not limited to, polymers, metals, alloys, or other suitable flexible materials known to those skilled in the art. In some embodiments, the material employed to manufacture the elongated shaft 302 may a piezoelectric material such as lead zirconate titanate (PZT) may be contemplated. In addition, other ceramic or piezoelectric materials known to those skilled in the art, such as barium titanate may also be used.

The modulation system 300 may further include one or more ablation transducers 316 disposed adjacent the distal end region 314 of the elongated shaft 302. The ablation transducers 316 may be formed from any suitable material such as, but not limited to, lead zirconate titanate (PZT). It is contemplated that other ceramic or piezoelectric materials may also be used. It is contemplated that the transducers 316 may have similar form and function to the transducers 208 discussed above. In some embodiments, there may be any number of ablation transducers 316 (one, two, three, four, or more) spaced about the circumference of the elongated shaft 302. This may allow for ablation of multiple radial locations about the body lumen simultaneously. In other embodiments, the ablation transducers 316 may comprise a focused or phased array of transducers. The array may be configured to be directed at a focus region such that multiple transducers are radiating energy at a common target region. It is further contemplated that the ablation transducers 316 may comprise a plurality of longitudinally spaced transducers.

The ablation transducers 316 may be connected to a control unit (such as control unit 18 in FIG. 1) by electrical conductor(s). In some embodiments, the electrical conductor(s) may be disposed within a lumen of the elongated shaft 302. In other embodiments, the electrical conductor(s) may extend along an outside surface of the elongated shaft 302. The electrical conductor(s) may provide electricity to the ablation transducers 316, which may then be converted into acoustic energy. The acoustic energy may be directed from the ablation transducers 316 in a direction generally perpendicular to the radiating surfaces of the transducers 316. As discussed above, acoustic energy radiates from the ablation transducers 316 in a pattern related to the shape of the transducers 316 and lesions formed during ablation take shape similar to contours of the pressure distribution.

The elongated shaft 302 may also be connected to a control unit and/or driver 310. The driver 310 may be adapted to provide and/or monitor the system 300 with one or more parameters such as, but not limited to, frequency for performing the desired ablation procedure. In some embodiments, the driver 310 may include an oscillator, which may provide mechanical movement to the elongated shaft or may propagate ultrasonic waves down the length of the elongated shaft 302. Exemplary oscillators may include a mechanical oscillator, acoustic oscillator, or other suitable oscillators known to those skilled in the art. In addition, those skilled in the art will appreciate that any other suitable drivers and/or energy sources may also be contemplated. While not explicitly shown, the driver 310 may be coupled to the elongated shaft 302 via an electrical connection or a mechanical connection. In certain instances, the connecting element may include an electrical conductor (not explicitly shown), adapted to supply power to the ablation transducers 316. This power may thus facilitate ablation of surrounding tissue within a vasculature.

In some embodiments, such as when a piezoelectric material is used for the elongated shaft 302, electricity may be provided to the elongated shaft 302, which may then be converted into vibrational energy as discussed above. The driver 310 may be configured to supply energy at a low frequency and at a higher amplitude relative to the frequency and amplitudes used for ablation to cause movement of the elongated shaft 302. The vibrational energy may cause the elongated shaft 302 to move back and forth in a direction 318 generally orthogonal to a longitudinal axis of the system 300. However, the elongated shaft 302 may vibrate in any other suitable directions known to those skilled in the art. The movement of the elongated shaft 302 may move the ablation transducers 316 back and forth within blood flow in the vessel, which may increase heat transfer from the transducers 316 to the blood, and thus cooling the ablation transducers 316. The movement of the elongated shaft 302 may also increase mixing of the blood, as well as reducing build-up of clots and/or other proteins.

The system 300 may be configured to operate at a first frequency for causing physical movement of the elongated shaft 302 and a second frequency for performing tissue modulation. Here, the first frequency may include a low frequency that may provide physical movement to the elongated shaft 302, thus providing cooling to the ablation transducers 316, as discussed above. It is contemplated that the first frequency may range from about 10 KHz to 200 KHz. It is further contemplated that the first frequency may include various other frequency ranges, as desired, based upon the physical affects produced. The second frequency may include a high frequency, which may ablate the target tissue. The second frequency may range from about 9-10 megahertz (MHz). It is contemplated that any desired frequency may be used, for example, from 1-20 MHz beyond. In general, the second frequency may be higher than the first frequency. The reverse configuration may also be utilized.

In other embodiments, such as when a piezoelectric material is not used for the elongated shaft 302, mechanical vibrations may be supplied over the length of the elongated shaft 302. For example, in some instances, the driver 310 may supply a mechanical or ultrasonic energy to the proximal end 312 of the elongated shaft 302. The mechanical or ultrasonic energy may cause the elongated shaft 302 to flex and/or vibrate along the entire length thereof. The vibrational energy may cause the elongated shaft 302 to move back and forth in a direction 318 generally orthogonal to a longitudinal axis of the system 300. However, the elongated shaft 302 may vibrate in any other suitable directions known to those skilled in the art. The movement of the elongated shaft 302 may move the ablation transducers 316 back and forth within blood flow in the vessel, which may increase heat transfer from the transducers 316 to the blood, and thus cooling the ablation transducers 316. The movement of the elongated shaft 302 may also increase mixing of the blood, as well as reducing build-up of clots and/or other proteins (e.g., along transducers 316).

The modulation system 300 may be advanced through the vasculature in any manner known in the art. For example, system 300 may include a guidewire lumen to allow the system 300 to be advanced over a previously located guidewire. In some embodiments, the modulation system 300 may be advanced, or partially advanced, within a guide sheath such as the catheter shaft 304. Once the ablation transducers 316 of the modulation system 300 have been placed adjacent to the desired treatment area, positioning mechanisms may be deployed, such as centering baskets, if so provided. While not explicitly shown, the ablation transducers 316 may be connected to a single control unit (such as control unit 18 in FIG. 1) by electrical conductors. As discussed above, the elongated shaft 302 may be connected to the driver 310 either electrically or mechanically. In some instances, the driver 310 may be configured to control the ablation transducers 316 as well. In other instances, the ablation transducers 316 and the elongated shaft 302 may be controlled by separate control units.

Once the modulation system 300 has been advanced to the treatment region, energy may be supplied to the ablation transducers 316. In some instances, energy may first be supplied to the ablation transducers 316. As the energy is radiated from the ablation transducers 316, the ablation transducers 316 may begin to heat. The modulation system 300 may use temperature sensors, or the monitoring means, to monitor the temperature or efficiency of the ablation transducers 316. Once the ablation transducers 316 have reached a predetermined criterion, vibrational energy may then be supplied to the elongated shaft 302 resulting in physical movement of the elongated shaft 302. As discussed above, the energy supplied to the elongated shaft may be electrical or mechanical. As the elongated shaft 302 moves, increased convection may transfer heat away from the ablation transducers 316. It is contemplated that energy may be supplied to the ablation transducers 316 and the elongated shaft 302 in an alternating fashion such that one is activated while the other is inactive. In other embodiments, the ablation transducers 316 and the elongated shaft 302 may be activated simultaneously. The amount of energy delivered to the ablation transducers 316 may be determined by the desired treatment as well as the feedback provided by the system 300.

In some instances, the elongate shaft 302 may be rotated and additional ablation can be performed at multiple locations around the circumference of the vessel. In some instances, a slow automated "rotisserie" rotation can be used to work around the circumference of the vessel, or a faster spinning can be used to simultaneously ablate around the entire circumference. The spinning can be accomplished with a micro-motor or by spinning a drive shaft. In some embodiments, ultrasound sensor information can be used to selectively turn on and off the ablation transducers 316 to warm any cool spots or accommodate for veins, or other tissue variations. The number of times the elongated shaft 302 is rotated at a given longitudinal location may be determined by the number and size of the ablation transducers 316 on the elongated shaft 302. Once a particular location has been ablated, it may be desirable to perform further ablation procedures at different longitudinal locations. Once the elongated shaft 302 has been longitudinally repositioned, energy may once again be delivered to the ablation transducers 316 and the elongated shaft 302. If necessary, the elongated shaft 302 may be rotated to perform ablation around the circumference of the vessel at each longitudinal location. This process may be repeated at any number of longitudinal locations desired. It is contemplated that in some embodiments, the system 300 may include ablation transducers at various positions along the length of the modulation system 300 such that a larger region may be treated without longitudinal displacement of the elongated shaft 302.

Figure 6:
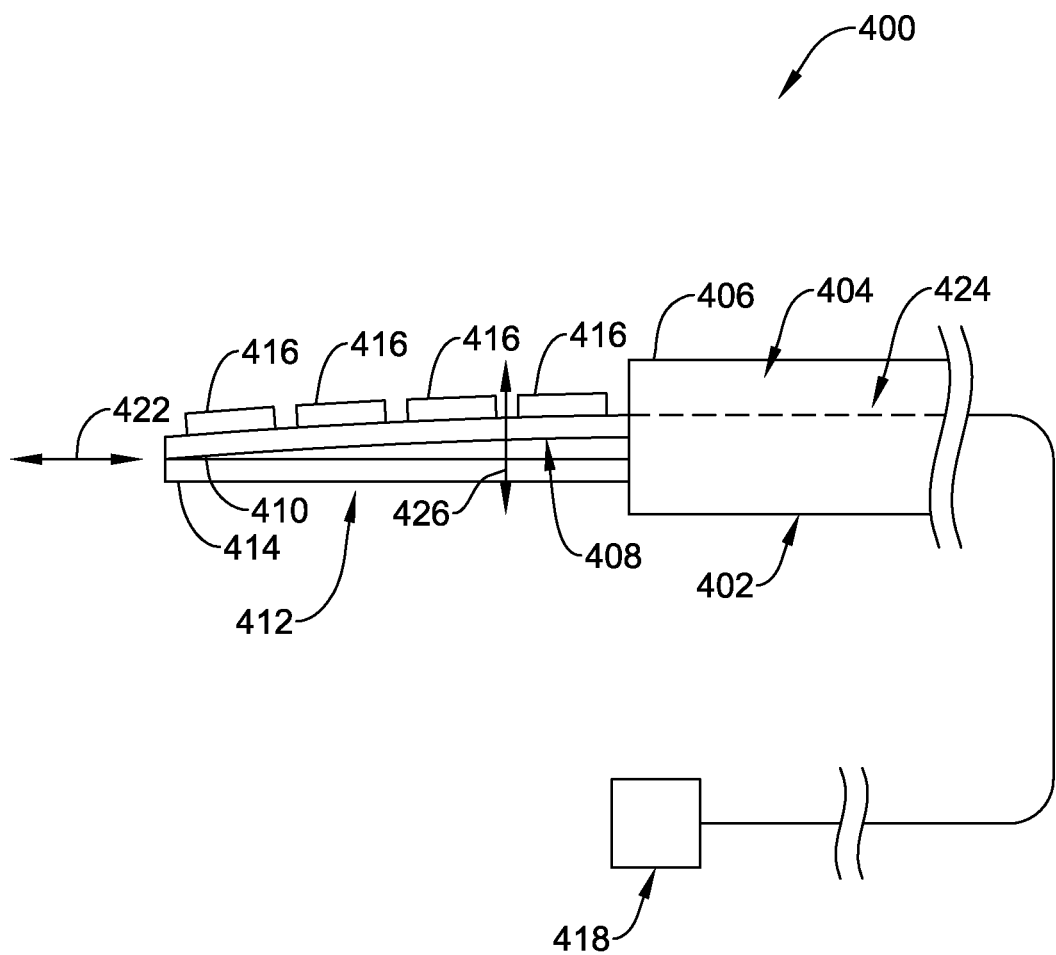
FIG. 6 illustrates a portion of another example intravascular nerve modulation system.

FIG. 6 illustrates a distal end of another illustrative intravascular nerve modulation system 400 that may be similar in function to other systems disclosed herein. As shown, the modulation system 400 may include a catheter shaft 402 having a distal end region 406. The catheter shaft 402 may extend proximally to a point configured to remain outside of a patient's body. The proximal end of the catheter shaft 402 may include a hub attached thereto for connecting other treatment devices or providing a port for facilitating other treatments. It is contemplated that the stiffness of the catheter shaft 402 may be modified to form a modulation system 400 for use in various vessel diameters and various locations within the vascular tree. In addition, the catheter shaft 402 may include a lumen 404 extending between the proximal end region (not shown) and the distal end region 406. The catheter shaft 402 may further include one or more lumens (not explicitly shown) in addition to lumen 404 extending therethrough. For example, the catheter shaft 402 may include a guidewire lumen and/or one or more auxiliary lumens. The lumens may be configured in any suitable way such as those ways commonly used for medical device. For example, the guidewire lumen may extend the entire length of the catheter shaft 402 such as in an over-the-wire catheter or may extend only along a distal portion of the catheter shaft 404 such as in a single operator exchange (SOE) catheter. These examples are not intended to be limiting, but rather examples of some possible configurations. While not explicitly shown, the modulation system 400 may further include temperature sensor/wire, an infusion lumen, radiopaque marker bands, fixed guidewire tip, a guidewire lumen, external sheath, and/or other components to facilitate the use and advancement of the system 400 within the vasculature.

The modulation system may further include a bar element 408 extending distally from the distal end region 406 of the catheter shaft 402. In some embodiments, the bar element 408 may include a long, thin bar-shaped element. It may be contemplated that other suitable shapes such as, but limited to rectangular, square, cylindrical, oval, irregular, and so forth may be used, as desired. The bar element 408 may have a proximal end (not explicitly shown) bonded, clamped or otherwise secured to the distal end region 406 of the catheter shaft 402. The bar element 408 may be formed of a piezoelectric material, such as, but not limited to, lead zirconate titanate (PZT) or barium titanate. It is contemplated that other ceramic or piezoelectric materials known to those skilled in the art may also be used. In some embodiments, the bar element 408 may include any suitable flexible biocompatible material such as, but are not limited to, polymers, metals, alloys, either in combination or alone.

The modulation system 400 may further include a tension member 412, such a tension ribbon or tension wire, disposed adjacent to the bar element 408. The tension member 412 may include a distal end 414 and a proximal end (not explicitly shown). In some instances, the proximal end of the tension member 412 may extend proximally to a location exterior to the patient's body. The distal end 414 of the tension member 412 may be bonded, clamped, or otherwise secured to the distal end 410 of the bar element.

The system 400 may include one or more ablation transducers 416 mounted on the distal end region bar element 408. The ablation transducers 416 may be formed from any suitable material such as, but not limited to, lead zirconate titanate (PZT). It is contemplated that other ceramic or piezoelectric materials may also be used. The transducers 416 may have similar form and function to the transducers 208 discussed above. In some embodiments, there may be any number of ablation transducers 416 (one, two, three, four, or more) spaced about the circumference of the bar element 408. This may allow for ablation of multiple radial locations about the body lumen simultaneously. In other embodiments, the ablation transducers 416 may comprise a focused or phased array of transducers. The array may be configured to be directed at a focus region such that multiple transducers are radiating energy at a common target region. It is further contemplated that the ablation transducers 416 may comprise a plurality of longitudinally spaced transducers.

The ablation transducers 416 may be connected to a control unit 418 by an electrical conductor(s). In some embodiments, the electrical conductor(s) may be disposed within a lumen of the catheter shaft 402. In other embodiments, the electrical conductor(s) may extend along an outside surface of the catheter shaft 402. The electrical conductor(s) may provide electricity to the ablation transducers 416, which may then be converted into acoustic energy. The acoustic energy may be directed from the ablation transducers 416 in a direction generally perpendicular to the radiating surfaces of the transducers 416. As discussed above, acoustic energy radiates from the ablation transducers 416 in a pattern related to the shape of the transducers 416 and lesions formed during ablation take shape similar to contours of the pressure distribution.

The bar element 408 may also be connected to a control unit 418 by electrical and/or mechanical means 424. In some embodiments, the connection 424 may be disposed within a lumen of the catheter shaft 402. In other embodiments, the connection 424 may extend along an outside surface of the catheter shaft 402. In some instances, the connection 424 may provide electricity to the bar element 408 which may then be converted into vibrational energy. In other embodiments, the control unit 418 may include an oscillator, which may provide mechanical movement, ultrasonic or other vibration, which may be transmitted along the length of the connection 424 to the bar element 408. Exemplary oscillators may include a mechanical oscillator, acoustic oscillator, or other suitable oscillators known to those skilled in the art. In addition, those skilled in the art will appreciate that any other suitable drivers and/or energy sources may also be contemplated. In certain instances, the control unit 418 may include an electrical conductor (not explicitly shown), adapted to supply power to the ablation transducers 416. This power may thus facilitate ablation of surrounding tissue within a vasculature.

In some cases, a driver creates vibration energy, which vibrates the bar element 408 through connection 424 and tension member 412. The vibrational energy may cause the bar element 408 to move back and forth in a direction 422 generally parallel to a longitudinal axis of the system 400. However, the bar element 408 may vibrate in any other suitable directions known to those skilled in the art. Longitudinal vibration of the distal end 410 of the bar element 408 in direction 422 combined with fixation of the proximal end of the bar element 408 at the distal end region 406 of catheter shaft 402 may cause the bar element 408 to flex and/or buckle and vibrate in a direction 426 generally orthogonal to a longitudinal axis of the system 400. This may cause the bar element 408 to flex and/or buckle in a direction 426 generally orthogonal to a longitudinal axis of the system 400. For example, a central region of the bar element 408 may bend back and forth to form concave and convex configurations. The movement of the bar element 408 may move the ablation transducers 416 back and forth within blood flow in the vessel which may increase heat transfer from the transducers 416 to the blood, and thus cooling the ablation transducers 416. The movement of the bar element 408 may also increase mixing of the blood, as well as reducing build-up of clots and/or other proteins (e.g., along transducers 416).

In some embodiments, the bar element 410 may be caused to flex and/or buckle in a direction 426 generally orthogonal to a longitudinal axis of the system 400 through actuation of the tension member 412. As discussed above, the tension member 412 may extend proximally through the lumen 404 of the catheter shaft to a location exterior to a patient's body. This may allow a user to manually actuate the tension member 412 in a piston-like push-pull manner to cause the bar element 410 to flex. As the tension member 412 is pulled proximally, the distal end 414 of the tension member 412 which is attached to the distal end of the bar element 410 may be moved proximally. This may cause the distal end of the bar element to move proximally as well. As the proximal end of the bar element 410 is fixedly secured, the bar element 410 is not longitudinally displaced with the tension member 412. As such, a central region of the bar element 408 may bend to form concave and/or convex configuration. As the tension member 412 is advanced distally, the bar element 408 may relax and return to a generally straight configuration. The movement of the bar element 408 may move the ablation transducers 416 back and forth within blood flow in the vessel which may increase heat transfer from the transducers 416 to the blood, and thus cooling the ablation transducers 416. The movement of the bar element 408 may also increase mixing of the blood, as well as reducing build-up of clots and/or other proteins (e.g., along transducers 416). It is further contemplated that the proximal end of the tension member 412 may be attached to a driver, such as driver 418, to automatically drive the push-pull actuation of the tension member 412.

The system 400 may be configured to operate at a first frequency for causing physical movement of the bar element 408 and a second frequency for performing tissue modulation. Here, the first frequency may include a low frequency that may provide physical movement to the bar element 408, thus providing cooling to the ablation transducers 416, as discussed above. It is contemplated that the first frequency may range from about 10 KHz to 200 KHz. It is further contemplated that the first frequency may include various other frequency ranges, as desired, based upon the physical affects produced. The second frequency may include a high frequency, which may ablate the target tissue. The second frequency may range from about 9-10 megahertz (MHz). It is contemplated that any desired frequency may be used, for example, from 1-20 MHz beyond. In general, the second frequency may be higher than the first frequency. The reverse configuration may also be utilized.

In other embodiments, such as when a piezoelectric material is not used for the bar element 408, mechanical vibrations may be supplied to the bar element 408. For example, in some instances, the control unit 418 may supply a mechanical or ultrasonic energy to the bar element 408. The mechanical or ultrasonic energy may cause the bar element 408 to flex and/or vibrate along the entire length thereof. The vibrational energy may cause the bar element 408 to move back and forth in a direction 422 generally parallel to a longitudinal axis of the system 400. However, the bar element 408 may vibrate in any other suitable directions known to those skilled in the art. As the bar element 408 is longitudinally secured at both its proximal end and distal end 410, longitudinal vibration of the bar element 408 is prevented. This may cause the bar element 408 to flex and/or buckle in a direction 426 generally orthogonal to a longitudinal axis of the system 400. For example, a central region of the bar element 408 may bend back and forth to form concave and convex configurations. The movement of the bar element 408 may move the ablation transducers 416 back and forth within blood flow in the vessel which may increase heat transfer from the transducers 416 to the blood, and thus cooling the ablation transducers 416. The movement of the bar element 408 may also increase mixing of the blood, as well as reducing build-up of clots and/or other proteins.

The modulation system 400 may be advanced through the vasculature in any manner known in the art. For example, system 400 may include a guidewire lumen to allow the system 400 to be advanced over a previously located guidewire. In some embodiments, the modulation system 400 may be advanced, or partially advanced, within a guide sheath, such as the sheath 16 shown in FIG. 1. Once the ablation transducers 416 of the modulation system 400 have been placed adjacent to the desired treatment area, positioning mechanisms may be deployed, such as centering baskets, if so provided. While not explicitly shown, the ablation transducers 416 may be connected to a control unit 418 by electrical conductors. As discussed above, the bar element 408 may be connected to the control unit 418 either electrically or mechanically. In some instances, the control unit 418 may be configured to control the ablation transducers 416 as well the bar element 408. In other instances, the ablation transducers 416 and the bar element 408 may be controlled by separate control units.

Once the modulation system 400 has been advanced to the treatment region, energy may be supplied to the ablation transducers 416. In some instances, energy may first be supplied to the ablation transducers 416. As the energy is radiated from the ablation transducers 416, the ablation transducers 416 may begin to heat. The modulation system 400 may use temperature sensors, or the monitoring means, to monitor the temperature or efficiency of the ablation transducers 416. Once the ablation transducers 416 have reached a predetermined criteria, energy may then be supplied to the bar element 408 resulting in physical movement of the bar element 408. As discussed above, the energy supplied to the elongated shaft may be electrical or mechanical. As the bar element 408 moves, increased convection may transfer heat away from the ablation transducers 416. It is contemplated that energy may be supplied to the ablation transducers 416 and the bar element 408 in an alternating fashion such that one is activated while the other is inactive. In other embodiments, the ablation transducers 416 and the bar element 408 may be activated simultaneously. The amount of energy delivered to the ablation transducers 416 may be determined by the desired treatment as well as the feedback provided by the system 400.

In some instances, the catheter shaft 402 may be rotated and additional ablation can be performed at multiple locations around the circumference of the vessel. In some instances, a slow automated "rotisserie" rotation can be used to work around the circumference of the vessel, or a faster spinning can be used to simultaneously ablate around the entire circumference. The spinning can be accomplished with a micro-motor or by spinning a drive shaft. In some embodiments, ultrasound sensor information can be used to selectively turn on and off the ablation transducers 416 to warm any cool spots or accommodate for veins, or other tissue variations. The number of times the catheter shaft 402 is rotated at a given longitudinal location may be determined by the number and size of the ablation transducers 416 on the bar element 408. Once a particular location has been ablated, it may be desirable to perform further ablation procedures at different longitudinal locations. Once the catheter shaft 402 has been longitudinally repositioned, energy may once again be delivered to the ablation transducers 416 and the bar element 408. If necessary, the catheter shaft 402 may be rotated to perform ablation around the circumference of the vessel at each longitudinal location. This process may be repeated at any number of longitudinal locations desired. It is contemplated that in some embodiments, the system 400 may include ablation transducers at various positions along the length of the modulation system 400 such that a larger region may be treated without longitudinal displacement of the catheter shaft 402.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. A tissue modulation system, comprising:
   an elongated shaft having a proximal end region and a distal end region;
   a control unit positioned adjacent the proximal end region of the elongated shaft;
   a bar element connected to the control unit and extending distally from the distal end region of the elongated shaft;
   a tension member extending adjacent to the bar element, the tension member configured to extend proximally to a location exterior to a patient's body during intravascular nerve modulation; and
   one or more ablation transducers affixed to the bar element and electrically connected to the control unit;
   wherein the control unit is configured to intermittently activate the bar element and the one or more ablation transducers in an alternating fashion;
   and wherein the control unit is configured to vibrate the bar element at a first frequency in a range of 10 kHz to 200 kHz.

2. The tissue modulation system of claim 1, wherein the one or more ablation transducers are configured to operate at a second frequency different from the first frequency.

3. The tissue modulation system of claim 1, wherein a proximal end of the bar element is attached to a distal end of the elongated shaft.

4. The tissue modulation system of claim 1, wherein the one or more ablation transducers are configured to radiate acoustic energy from at least one side surface.

5. The tissue modulation system of claim 1, wherein the one or more ablation transducers affixed to the bar element are positioned on a side of the bar element opposite the tension member.

6. The tissue modulation system of claim 1, wherein the control unit is configured to vibrate the bar element in a direction generally parallel to a longitudinal axis of the catheter shaft.

7. The tissue modulation system of claim 6, wherein vibration of the bar element causes the bar element to buckle in a direction generally orthogonal to the longitudinal axis of the catheter shaft.

8. A tissue modulation system, comprising:
a catheter shaft having a proximal end region, a distal end region, and a lumen extending therebetween;
a control unit positioned adjacent the proximal end region of the catheter shaft;
a bar element having a proximal end region and a distal end region, the bar element disposed adjacent to the distal end region of the catheter shaft;
a tension member extending adjacent to the bar element, the tension member configured to extend proximally to a location exterior to a patient's body during tissue modulation; and
one or more ablation transducers secured to the distal end region of the bar element and electrically connected to the control unit;
wherein the bar element is connected to the control unit;
wherein the control unit is configured to vibrate the bar element in a direction generally parallel to a longitudinal axis of the catheter shaft;
wherein the control unit is configured to intermittently activate the bar element and the one or more ablation transducers in an alternating fashion; and
wherein the control unit is configured to vibrate the bar element at a first frequency in a range of 10 kHz to 200 kHz.

9. The tissue modulation system of claim 8, wherein the control unit is a mechanical oscillator or an ultrasonic oscillator.

10. The tissue modulation system of claim 8, wherein the tension member is fixedly secured to a distal end of the bar element.

11. The tissue modulation system of claim 8, wherein proximal and distal actuation of the tension member causes the bar element to flex and relax.

12. The tissue modulation system of claim 11, wherein the bar element is configured to be flexed in a direction generally orthogonal to a longitudinal axis of the catheter shaft.

13. The tissue modulation system of claim 10, wherein the tension member limits longitudinal vibration of the bar element causing a central portion of the bar element to buckle.

14. The tissue modulation system of claim 8, wherein the one or more ablation transducers secured to the distal end region of the bar element are positioned on a side of the bar element opposite the tension member.

15. The tissue modulation system of claim 8, wherein vibration of the bar element causes the bar element to buckle in a direction generally orthogonal to the longitudinal axis of the catheter shaft.

* * * * *